(12) United States Patent
Bowen et al.

(10) Patent No.: US 12,349,242 B2
(45) Date of Patent: Jul. 1, 2025

(54) CARTRIDGE-BASED HEAT NOT BURN VAPORIZER

(71) Applicant: JUUL Labs, Inc., Washington, DC (US)

(72) Inventors: Adam Bowen, San Mateo, CA (US); James Monsees, San Francisco, CA (US)

(73) Assignee: JUUL Labs, Inc., Washington, DC (US)

( * ) Notice: Subject to any disclaimer, the term of this patent is extended or adjusted under 35 U.S.C. 154(b) by 0 days.

(21) Appl. No.: 18/229,375

(22) Filed: Aug. 2, 2023

(65) Prior Publication Data
US 2023/0380018 A1    Nov. 23, 2023

Related U.S. Application Data

(63) Continuation of application No. 17/900,486, filed on Aug. 31, 2022, now abandoned, which is a
(Continued)

(51) Int. Cl.
*H05B 3/34*    (2006.01)
*A24B 15/167*   (2020.01)
(Continued)

(52) U.S. Cl.
CPC ............ *H05B 3/34* (2013.01); *A24B 15/167* (2016.11); *A24F 40/42* (2020.01); *A24F 40/20* (2020.01);
(Continued)

(58) Field of Classification Search
None
See application file for complete search history.

(56) References Cited

U.S. PATENT DOCUMENTS

| | | |
|---|---|---|
| 3,373,915 A | 3/1968 | Anderson et al. |
| 3,559,655 A | 2/1971 | Briskin et al. |

(Continued)

FOREIGN PATENT DOCUMENTS

| | | |
|---|---|---|
| CA | 3010559 A1 | 7/2017 |
| CN | 102753047 A | 10/2012 |

(Continued)

OTHER PUBLICATIONS

Guo, et al. (Mar. 31, 2016) "Heat Transfer Performance of Atomizer of Electronic Cigar", Popular Science and Technology, 18(3):52-54.
(Continued)

*Primary Examiner* — Ross N Gushi
(74) *Attorney, Agent, or Firm* — Mintz, Levin, Cohn, Ferris, Glovsky and Popeo, P.C.

(57) ABSTRACT

A vaporizer cartridge configured to efficiently and effectively heat a non-liquid source material that includes a vaporizable material is described. The cartridge may include a heating element including an electrically resistive material and may be configured to vaporize the vaporizable material by delivery of heat to the vaporizable material. The cartridge may include a cartridge contact in electrical communication with the electrically resistive material. The cartridge contact may be configured to couple to a vaporizer contact positioned proximate to a cartridge coupling feature to allow electrical power to pass from the vaporizer device through the electrically resistive material. The electrical power may cause heating of the electrically resistive material and the vaporizable material to result in generation of an aerosol for inhalation by a user. Related systems, methods, and articles of manufacture are also described.

20 Claims, 11 Drawing Sheets

Related U.S. Application Data continuation of application No. 16/528,494, filed on Jul. 31, 2019, now Pat. No. 11,464,082.

(60) Provisional application No. 62/712,919, filed on Jul. 31, 2018.

(51) Int. Cl.
*A24F 40/42* (2020.01)
*A24F 40/20* (2020.01)

(52) U.S. Cl.
CPC .. *H05B 2203/007* (2013.01); *H05B 2203/013* (2013.01); *H05B 2203/021* (2013.01)

(56) References Cited

U.S. PATENT DOCUMENTS

| | | |
|---|---|---|
| 3,584,631 A | 6/1971 | Halter et al. |
| 4,708,151 A | 11/1987 | Shelar |
| 5,042,509 A | 8/1991 | Banerjee et al. |
| 5,065,776 A | 11/1991 | Lawson et al. |
| 5,249,586 A | 10/1993 | Morgan et al. |
| 5,479,948 A | 1/1996 | Counts et al. |
| 7,726,320 B2 | 6/2010 | Robinson et al. |
| 8,490,629 B1 | 7/2013 | Shenassa et al. |
| 8,671,952 B2 | 3/2014 | Winterson et al. |
| 8,869,792 B1 | 10/2014 | Lee |
| 8,991,402 B2 | 3/2015 | Bowen et al. |
| 9,408,416 B2 | 8/2016 | Monsees et al. |
| 9,603,389 B2 | 3/2017 | Chen |
| 9,943,114 B2 * | 4/2018 | Batista .................... A24F 40/70 |
| 10,512,285 B2 | 12/2019 | Kuczaj |
| 10,729,179 B2 | 8/2020 | Atkins et al. |
| 11,129,414 B2 | 9/2021 | Atkins et al. |
| 11,147,128 B2 | 10/2021 | Qiu |
| 11,197,497 B2 | 12/2021 | Lee et al. |
| 11,464,082 B2 | 10/2022 | Jobanputra et al. |
| 11,700,874 B2 | 7/2023 | Alizon et al. |
| 12,010,782 B2 | 6/2024 | Horrod et al. |
| 12,156,538 B2 | 12/2024 | Leah et al. |
| 2004/0055613 A1 | 3/2004 | Horian |
| 2005/0268911 A1 | 12/2005 | Cross et al. |
| 2006/0032501 A1 | 2/2006 | Hale et al. |
| 2007/0221234 A1 | 9/2007 | Beckstead |
| 2007/0283972 A1 | 12/2007 | Monsees et al. |
| 2008/0092912 A1 | 4/2008 | Robinson et al. |
| 2009/0126746 A1 | 5/2009 | Strickland et al. |
| 2009/0260642 A1 | 10/2009 | Monsees et al. |
| 2010/0024834 A1 | 2/2010 | Oglesby et al. |
| 2011/0041861 A1 | 2/2011 | Sebastian et al. |
| 2011/0226236 A1 | 9/2011 | Buchberger |
| 2011/0290267 A1 | 12/2011 | Yamada et al. |
| 2013/0042865 A1 | 2/2013 | Monsees et al. |
| 2014/0301721 A1 | 10/2014 | Ruscio et al. |
| 2014/0366898 A1 | 12/2014 | Monsees et al. |
| 2015/0272218 A1 | 10/2015 | Chen |
| 2015/0335070 A1 | 11/2015 | Sears et al. |
| 2016/0073692 A1 | 3/2016 | Alarcon et al. |
| 2016/0120222 A1 | 5/2016 | Bagai et al. |
| 2016/0120225 A1 | 5/2016 | Mishra et al. |
| 2016/0120227 A1 | 5/2016 | Levitz et al. |
| 2016/0295922 A1 | 10/2016 | John et al. |
| 2016/0309782 A1 | 10/2016 | Malgat et al. |
| 2016/0338412 A1 | 11/2016 | Monsees et al. |
| 2017/0035116 A1 | 2/2017 | Batista |
| 2017/0055575 A1 | 3/2017 | Wilke et al. |
| 2017/0055580 A1 | 3/2017 | Blandino et al. |
| 2017/0071250 A1 | 3/2017 | Mironov et al. |
| 2017/0143041 A1 | 5/2017 | Batista et al. |
| 2017/0156403 A1 | 6/2017 | Gill et al. |
| 2017/0164657 A1 | 6/2017 | Batista |
| 2018/0027877 A1 | 2/2018 | Tucker et al. |
| 2018/0027883 A1 | 2/2018 | Zuber et al. |
| 2018/0084823 A1 | 3/2018 | Fuisz et al. |
| 2018/0110263 A1 | 4/2018 | Borkovec et al. |
| 2018/0132534 A1 | 5/2018 | Reevell |
| 2018/0228216 A1 | 8/2018 | Saygili |
| 2018/0295881 A1 | 10/2018 | Mironov et al. |
| 2018/0325179 A1 | 11/2018 | Li et al. |
| 2019/0001077 A1 | 1/2019 | Xu et al. |
| 2019/0037921 A1 | 2/2019 | Kennedy et al. |
| 2019/0098930 A1 | 4/2019 | Fallon et al. |
| 2019/0124982 A1 | 5/2019 | Atkins et al. |
| 2019/0166913 A1 | 6/2019 | Trzecieski |
| 2019/0191769 A1 | 6/2019 | Qiu |
| 2019/0200674 A1 | 7/2019 | Tucker et al. |
| 2019/0200677 A1 | 7/2019 | Chong et al. |
| 2019/0208827 A1 | 7/2019 | Mironov et al. |
| 2020/0107585 A1 | 4/2020 | Atkins et al. |
| 2020/0113245 A1 | 4/2020 | Rosser et al. |
| 2020/0120993 A1 | 4/2020 | Atkins et al. |
| 2020/0324066 A1 | 10/2020 | Potter |
| 2021/0186113 A1 | 6/2021 | Lee |
| 2021/0321672 A1 | 10/2021 | Wilke et al. |
| 2021/0386120 A1 | 12/2021 | Gill |
| 2022/0030953 A1 | 2/2022 | Woods et al. |
| 2022/0046997 A1 | 2/2022 | Atkins et al. |
| 2022/0095685 A1 | 3/2022 | Atkins et al. |
| 2022/0104550 A1 | 4/2022 | Mao et al. |
| 2022/0160040 A1 | 5/2022 | Zhang et al. |

FOREIGN PATENT DOCUMENTS

| | | |
|---|---|---|
| CN | 103783674 A | 5/2014 |
| CN | 105764367 A | 7/2016 |
| CN | 106307622 A | 1/2017 |
| CN | 106572705 A | 4/2017 |
| CN | 106659247 A | 5/2017 |
| CN | 106659250 A | 5/2017 |
| CN | 106858726 A | 6/2017 |
| CN | 107772540 A | 3/2018 |
| CN | 111432670 A | 7/2020 |
| CN | 113163855 A | 7/2021 |
| EP | 2394520 A1 | 12/2011 |
| EP | 3420829 A1 | 1/2019 |
| EP | 3664631 A2 | 6/2020 |
| EP | 3829366 A1 | 6/2021 |
| GB | 2527597 A | 12/2015 |
| GB | 2547699 A | 8/2017 |
| GB | 2568411 B | 8/2019 |
| JP | S5138499 A | 3/1976 |
| JP | 2001507576 A | 6/2001 |
| JP | 2010506594 A | 3/2010 |
| JP | 2010517568 A | 5/2010 |
| JP | 2010178730 A | 8/2010 |
| JP | 2013516159 A | 5/2013 |
| JP | 2015509709 A | 4/2015 |
| JP | 2016538847 A | 12/2016 |
| JP | 2016538850 A | 12/2016 |
| JP | 2017018146 A | 1/2017 |
| JP | 2017529848 A | 10/2017 |
| JP | 2017529896 A | 10/2017 |
| JP | 2017533732 A | 11/2017 |
| JP | 2020536536 A | 12/2020 |
| KR | 20120008751 U | 12/2012 |
| KR | 10-2016-0112769 A | 9/2016 |
| RU | 2602053 C2 | 11/2016 |
| RU | 2604313 C2 | 12/2016 |
| RU | 2629878 C1 | 9/2017 |
| RU | 2655239 C2 | 5/2018 |
| WO | WO-2006120570 A2 | 11/2006 |
| WO | WO-2011079932 A1 | 7/2011 |
| WO | WO-2013060743 A2 | 5/2013 |
| WO | WO-2015082651 A1 | 6/2015 |
| WO | WO-2015155289 A1 | 10/2015 |
| WO | WO-2015179388 A1 | 11/2015 |
| WO | WO-2016005533 A1 | 1/2016 |
| WO | WO-2016062777 A1 | 4/2016 |
| WO | WO-2016079589 A1 | 5/2016 |
| WO | WO-2016162446 A1 | 10/2016 |
| WO | WO-2017072148 A1 | 5/2017 |
| WO | WO-2017122196 A1 | 7/2017 |
| WO | WO-2017129617 A1 | 8/2017 |
| WO | WO-2017207418 A1 | 12/2017 |

(56) References Cited

FOREIGN PATENT DOCUMENTS

| WO | WO-2017207419 A1 | 12/2017 |
|---|---|---|
| WO | WO-2017207582 A1 | 12/2017 |
| WO | WO-2018019578 A1 | 2/2018 |
| WO | WO-2018041065 A1 | 3/2018 |
| WO | WO-2018122389 A1 | 7/2018 |
| WO | WO-2018122978 A1 | 7/2018 |
| WO | WO-2018206615 A2 | 11/2018 |
| WO | WO-2019057942 A1 | 3/2019 |
| WO | WO-2019073237 A1 | 4/2019 |
| WO | WO-2019122015 A1 | 6/2019 |
| WO | WO-2020028591 A1 | 2/2020 |
| WO | WO-2020239599 A1 | 12/2020 |

OTHER PUBLICATIONS (2015) "Property Tables and Charts (SI Units)", Wright State University, p. 865-892.

* cited by examiner

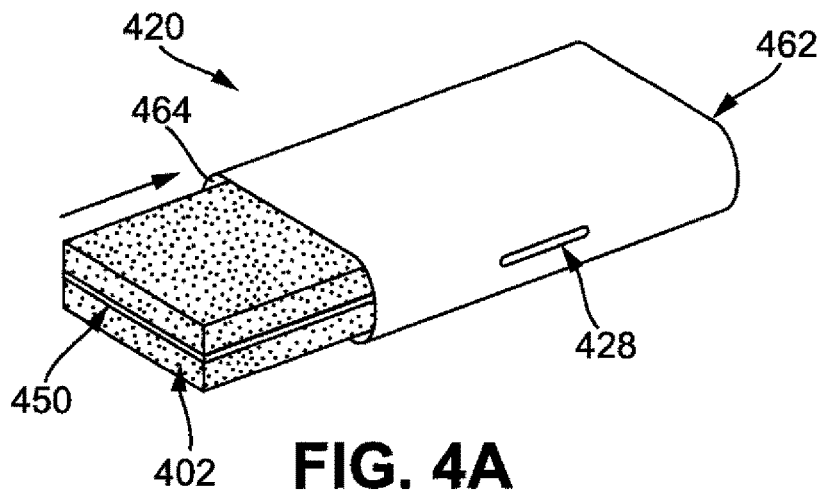
FIG. 4A
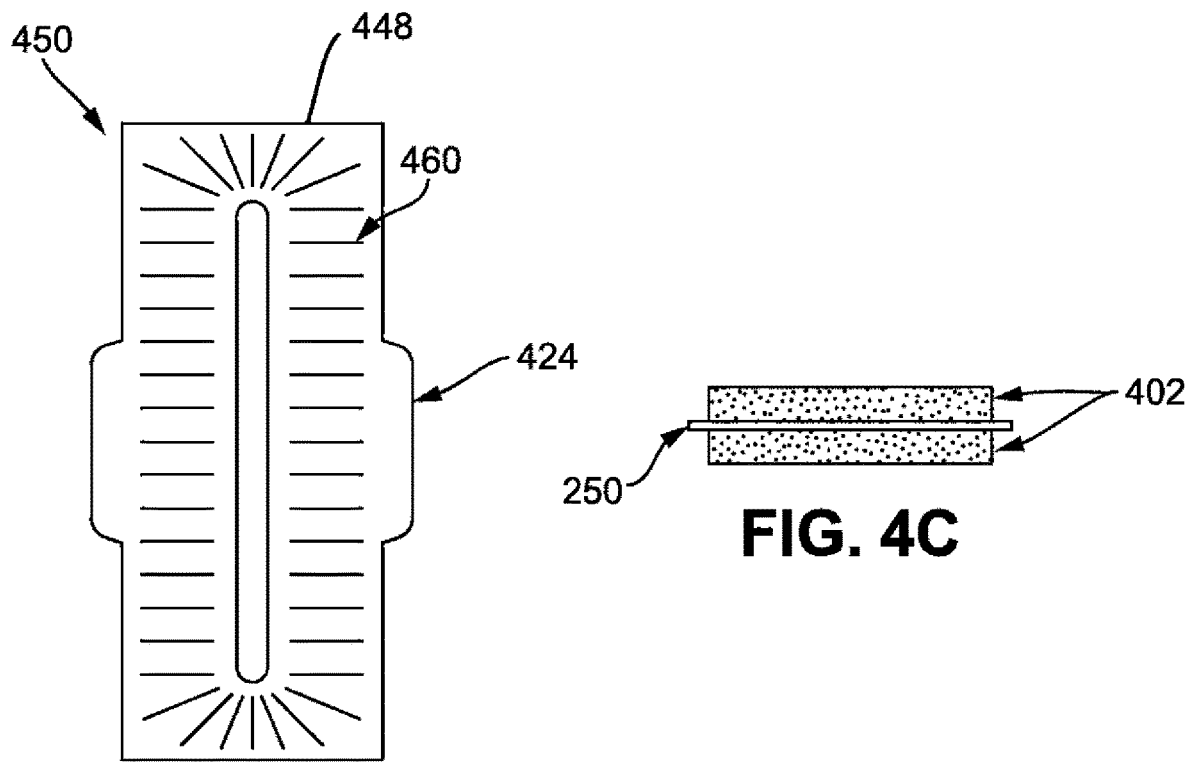
FIG. 4B   FIG. 4C

CARTRIDGE-BASED HEAT NOT BURN VAPORIZER

CROSS REFERENCE

The present application is a continuation application of U.S. patent application Ser. No. 17/900,486 entitled "Cartridge-Based Heat Not Burn Vaporizer" and filed on Aug. 31, 2022, which is a continuation of U.S. patent application Ser. No. 16/528,494 entitled "Cartridge-Based Heat Not Burn Vaporizer" and filed on Jul. 31, 2019, now issued as U.S. Pat. No. 11,464,082, which claims priority to U.S. Provisional Patent Application No. 62/712,919 entitled "Cartridge-Based Heat Not Burn Vaporizer" and filed Jul. 31, 2018, the disclosures of which are hereby incorporated by reference in their entirety.

TECHNICAL FIELD

The subject matter described herein relates to vaporizer devices, including a system for heating vaporizable material to generate an inhalable aerosol.

BACKGROUND

Vaporizing devices, including electronic vaporizers or e-vaporizer devices, allow the delivery of vapor containing one or more active ingredients to a user by inhalation of the vapor. Electronic vaporizer devices are gaining increasing popularity both for prescriptive medical use, in delivering medicaments, and for consumption of tobacco and other plant-based smokeable materials, such as *cannabis*, including solid (e.g., loose-leaf) materials, solid/liquid (e.g., suspensions, liquid-coated) materials, wax extracts, and pre-filled pods (cartridges, wrapped containers, etc.) of such materials. Electronic vaporizer devices in particular may be portable, self-contained, and convenient for use.

In some embodiments, vaporizer cartridges configured to heat vaporizable material (e.g., plant material such as tobacco leaves and/or parts of tobacco leaves) require higher temperatures for the inner tobacco regions to reach the minimum required temperature for vaporization. As a result, burning the vaporizable material at these high peak temperatures can produce toxic bi-products (e.g., chemical elements or chemical compounds).

SUMMARY

Aspects of the current subject matter relate to a cartridge for a vaporizer device. In some embodiments, the cartridge may include a chamber configured to contain a non-liquid vaporizable material. The cartridge may include a heating element. The heating element may include an electrically resistive material and may be configured to vaporize the vaporizable material by delivery of heat to the vaporizable material, wherein at least a portion of the heating element may define a part of the chamber and/or may be contained within the chamber.

The cartridge may include a cartridge contact in electrical communication with the electrically resistive material. The cartridge contact may be configured to couple to a vaporizer contact positioned proximate to a cartridge coupling feature to allow electrical power to pass from the vaporizer device through the electrically resistive material. The electrical power may cause heating of the electrically resistive material and the vaporizable material to result in generation of an aerosol for inhalation by a user.

In some variations, one or more of the following features can optionally be included in any feasible combination. The heating element may include the cartridge contact. The cartridge may include a sheet of thermally conductive, electrically resistive material. The sheet of thermally conductive, electrically resistive material may include at least one of a flexible material, a deformable material, and a rigid material. The sheet of thermally conductive, electrically resistive material may include at least one perforation. The sheet of thermally conductive, electrically resistive material may include at least one extension extending away from at least one of a top surface of the sheet of thermally conductive, electrically resistive material and a bottom surface of the sheet of thermally conductive, electrically resistive material.

The sheet of thermally conductive, electrically resistive material may include a first area having a first density of perforations and a second area having a second density of perforations that is greater than a first density of perforations.

The heating element may include a non-electrically conductive area. The heating element may include a flexible printed circuit including the electrically resistive material traced on a flexible material, and wherein the traced electrically resistive material may form a plurality of series heaters. The plurality of series heaters may be positioned in parallel. The heating element may include a flexible material with the electrically resistive material extending along a length of the flexible material.

The cartridge may include a housing. The housing may include a non-electrically conductive material and may contain at least a part of the chamber. The vaporizable material may include nicotine.

In some embodiments, a system for a generating an inhalable aerosol may include the cartridge. The cartridge may include a chamber configured to contain a non-liquid vaporizable material. The cartridge may include a heating element. The heating element may include an electrically resistive material and may be configured to vaporize the vaporizable material by delivery of heat to the vaporizable material, wherein at least a portion of the heating element defines a part of the chamber and/or may be contained within the chamber. The cartridge may include a cartridge contact in electrical communication with the electrically resistive material. The cartridge contact may be configured to couple to a vaporizer contact positioned proximate to a cartridge coupling feature to allow electrical power to pass from the vaporizer device through the electrically resistive material. The electrical power may cause heating of the electrically resistive material and the vaporizable material to result in generation of an aerosol for inhalation by a user The system may include a device body. The device body may include a cartridge receptacle for receiving the cartridge. The device body may include a vaporizer contact configured to mate with the cartridge contact when the cartridge is inserted into the cartridge receptacle to provide an electrically conductive pathway between a power source in the device body and the heating element of the cartridge.

In some embodiments, a method for generating an inhalable aerosol may include coupling a cartridge contact of a vaporizer cartridge to a vaporizer contact of a vaporizer device body to provide an electrically conductive pathway between a power source of the vaporizer device body and a heating element of the vaporizer cartridge. The electrically conductive pathway may allow the power source to cause heating of an electrically resistive material of the heating element and the vaporizable material contained in a chamber of the cartridge.

The method may include heating the heating element to vaporize the vaporizable material and form an aerosol for inhalation, wherein the heating element defines at least a part of the chamber and/or is contained within the chamber of the vaporizer cartridge.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 4A illustrates a top perspective view of another embodiment of a vaporizer cartridge including another embodiment of a heating element in contact with non-liquid vaporizable material.

FIG. 4B illustrates a top view of the heating element of the vaporizer cartridge of FIG. 4A;

FIG. 4C illustrates a side view of the heating element of FIG. 4B with a sheet of non-liquid vaporizable material coupled to top and bottom sides of the heating element;

When practical, similar reference numbers denote similar structures, features, or elements.

DETAILED DESCRIPTION

Implementations of the current subject matter include devices relating to vaporizing one or more materials for inhalation by a user. For example, various embodiments of vaporizer cartridges, such as single-use disposable cartridges, having a variety of heater element embodiments are described herein. Such vaporizer cartridges can be configured for use with non-liquid vaporizable material, such as loose-leaf tobacco. The various heater element embodiments described herein can improve the efficiency and quality of heating of the vaporizable material, such as heating the vaporizable material within an optimal heating range. Such optimal heating range includes a temperature that is hot enough to vaporize the vaporizable material into an aerosol for inhalation, while also heating below a temperature that produces harmful or potentially harmful byproducts.

In some embodiments, the heating elements described herein can achieve the optimal heating range at a rate that allows a user to have an enjoyable user experience (e.g., not have to wait a long time for the heating element to reach a temperature in the optimal heating range, etc.). In some embodiments, the vaporizer cartridges including such heating elements can be cost effectively manufactured, thereby making them economically feasible as single-use disposable cartridges. Various vaporizer cartridges and heating elements including one or more of the above features are described in greater detail below.

As noted above, vaporizable material used with a vaporizer may optionally be provided within a cartridge (e.g., a part of the vaporizer that contains the vaporizable material or a source substance that includes the vaporizable material in a reservoir or other container and that can be refillable when empty or disposable in favor of a new cartridge containing additional vaporizable material of a same or different type). A vaporizer may be a cartridge-using vaporizer, a cartridge-less vaporizer, or a multi-use vaporizer capable of use with or without a cartridge. For example, a multi-use vaporizer may include a heating chamber (e.g., an oven) configured to receive a source substance containing a vaporizable material directly in the heating chamber and also to receive a vaporizer cartridge 120 or other replaceable device having a reservoir, a volume, or the like for at least partially containing a usable amount of a source substance containing or including the vaporizable material.

In various implementations, a vaporizer may be configured for use with a solid vaporizable material, which may include a plant material that emits some part of the plant material as the vaporizable material (e.g., such that some part of the plant material remains as waste after the vaporizable material is emitted for inhalation by a user) or optionally can be a solid form of the vaporizable material itself (e.g., a "wax") such that all of the solid material can eventually be vaporized for inhalation.

Figure 1:
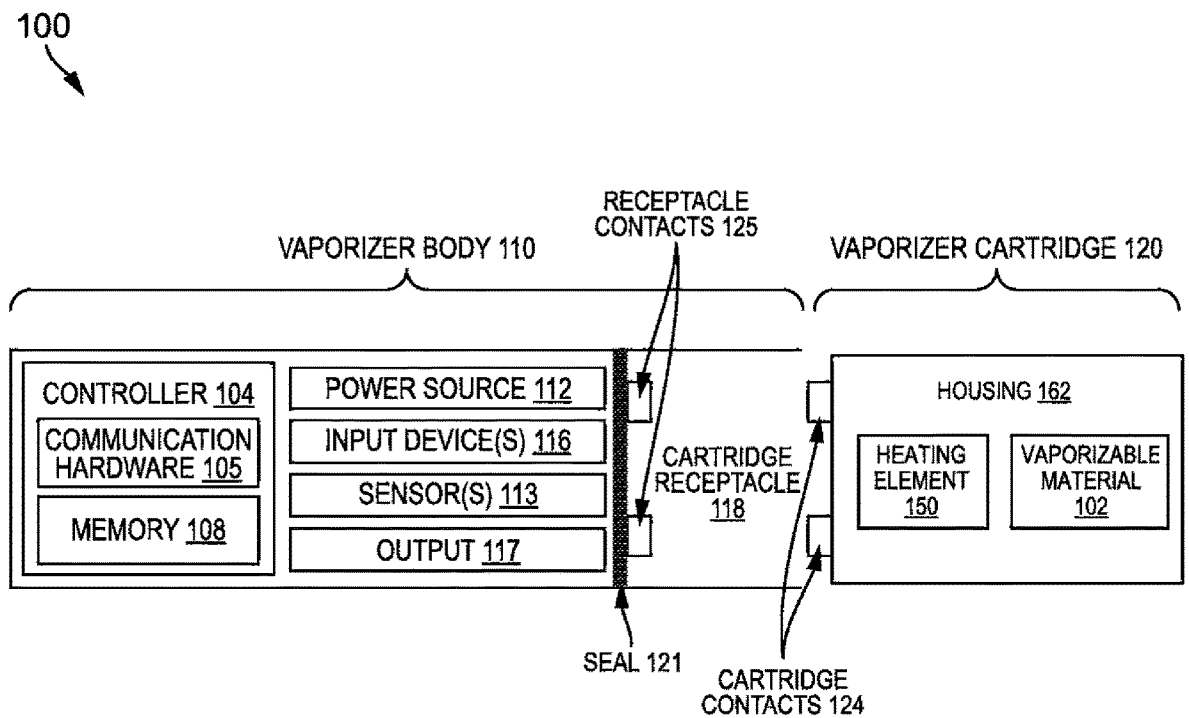
FIG. 1 illustrates a block diagram of a vaporizer consistent with implementations of the current subject matter.

Referring to the block diagram of FIG. 1, a vaporizer 100 typically includes a power source 112 (such as a battery which may be a rechargeable battery), and a controller 104 (e.g., a processor, circuitry, etc. capable of executing logic) for controlling delivery of heat to a heating element to cause a vaporizable material to be converted from a condensed form (e.g., a solid, a liquid, a solution, a suspension, a part of an at least partially unprocessed plant material, etc.) to the gas phase. The controller 104 may be part of one or more printed circuit boards (PCBs) consistent with certain implementations of the current subject matter. In the current subject matter, which generally relates to devices for producing an inhalable aerosol through heating of a source substance without burning it, the condensed form is typically a plant-based material, at least part of which is a vaporizable material capable of being converted to vapor under heating of the plant-based material.

After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which can form some or all of an inhalable dose provided by the vaporizer 100 for a given puff or draw on the vaporizer. It will be understood that the interplay between gas and condensed phases in an aerosol generated by a vaporizer can be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc. may affect one or more physical parameters of an aerosol. In some vaporizers, and particularly for vaporizers for delivery of more volatile vaporizable materials, the inhalable dose may exist predominantly in the gas phase (i.e., formation of condensed phase particles may be very limited).

As noted above, vaporizers consistent with implementations of the current subject matter may also or alternatively be configured to create an inhalable dose of gas-phase and/or aerosol-phase vaporizable material via heating of a non-liquid source substance containing or including a vaporizable material, such as for example a solid-phase vaporizable material or plant material (e.g., tobacco leaves and/or parts of tobacco leaves) containing the vaporizable material. In such vaporizers, a heating element may be part of or otherwise incorporated into or in thermal contact with the walls of an oven or other heating chamber into which the non-liquid source substance that contains or includes a vaporizable material is placed. Alternatively, a heating element or elements may be used to heat air passing through or past the non-liquid source substance to cause convective heating of the non-liquid vaporizable material. In still other examples, a heating element or elements may be disposed in intimate contact with plant material such that direct thermal conduction heating of the source substance occurs from within a mass of the source substance (e.g., as opposed to only by conduction inward from walls of an oven). Such non-liquid vaporizable materials may be used with cartridge using or cartridge less vaporizers.

The heating element can be or include one or more of a conductive heater, a radiative heater, and a convective heater. One type of heating element is a resistive heating element, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer can include a heating element that includes resistive coil or other heating element wrapped around, positioned within, integrated into a bulk shape of, pressed into thermal contact with, or otherwise arranged to deliver heat to a mass of a source substance (e.g., plant based-substance such as tobacco) that contains the vaporizable material. Throughout the current disclosure, "source substance" generally refers to the part of a plant-based material (or other condensed form of a plant material or other material that may release vaporizable material without being burned) that contains vaporizable materials that are converted to vapor and/or aerosol for inhalation. Other heating element, and/or atomizer assembly configurations are also possible, as discussed further below.

The heating element may be activated (e.g., a controller, which is optionally part of a vaporizer body as discussed below, may cause current to pass from the power source through a circuit including the resistive heating element, which is optionally part of a vaporizer cartridge as discussed below), in association with a user puffing (e.g., drawing, inhaling, etc.) on a mouthpiece of the vaporizer to cause air to flow from an air inlet, along an airflow path that passes the heating element and an associated mass of the source substance, optionally through one or more condensation areas or chambers, to an air outlet in the mouthpiece. Incoming air passing along the airflow path passes over, through, etc. the heating element and the source substance, where gas phase vaporizable material is entrained into the air. As noted above, the entrained gas-phase vaporizable material may condense as it passes through the remainder of the airflow path such that an inhalable dose of the vaporizable material in an aerosol form can be delivered from the air outlet (e.g., in a mouthpiece for inhalation by a user).

Activation of the heating element may be caused by automatic detection of the puff based on one or more of signals generated by one or more sensors 113, such as for example a pressure sensor or sensors disposed to detect pressure along the airflow path relative to ambient pressure (or optionally to measure changes in absolute pressure), one or more motion sensors of the vaporizer, one or more flow sensors of the vaporizer, a capacitive lip sensor of the vaporizer; in response to detection of interaction of a user with one or more input devices 116 (e.g., buttons or other tactile control devices of the vaporizer 100), receipt of signals from a computing device in communication with the vaporizer; and/or via other approaches for determining that a puff is occurring or imminent.

As alluded to in the previous paragraph, a vaporizer consistent with implementations of the current subject matter may be configured to connect (e.g., wirelessly or via a wired connection) to a computing device (or optionally two or more devices) in communication with the vaporizer. To this end, the controller 104 may include communication hardware 105. The controller 104 may also include a memory 108. A computing device can be a component of a vaporizer system that also includes the vaporizer 100, and can include its own communication hardware, which can establish a wireless communication channel with the communication hardware 105 of the vaporizer 100. For example, a computing device used as part of a vaporizer system may include a general-purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer can also include one or more output 117 features or devices for providing information to the user. For example, the output 117 can include one or more light emitting diodes (LED) configured to provide feedback to a user based on a status and/or mode of operation of the vaporizer 100.

A computing device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, etc.), controlling nicotine delivery (e.g., switching between nicotine and non-nicotine vaporizable material, adjusting an amount of nicotine delivered, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g., games, social media communications, interacting with one or more groups, etc.) with other users, or the like. The terms "sessioning", "session", "vaporizer session," or "vapor session," are used generically to refer to a period devoted to the use of the vaporizer. The period can include a time period, a number of doses, an amount of vaporizable material, and/or the like.

In the example in which a computing device provides signals related to activation of the resistive heating element, or in other examples of coupling of a computing device with a vaporizer for implementation of various control or other functions, the computing device executes one or more computer instructions sets to provide a user interface and underlying data handling. In one example, detection by the computing device of user interaction with one or more user interface elements can cause the computing device to signal the vaporizer 100 to activate the heating element, either to a full operating temperature for creation of an inhalable dose of vapor/aerosol. Other functions of the vaporizer may be controlled by interaction of a user with a user interface on a computing device in communication with the vaporizer.

The temperature of a resistive heating element of a vaporizer may depend on a number of factors, including an amount of electrical power delivered to the resistive heating element and/or a duty cycle at which the electrical power is delivered, conductive heat transfer to other parts of the electronic vaporizer and/or to the environment, latent heat losses due to vaporization of a vaporizable material from the atomizer as a whole, and convective heat losses due to airflow (e.g., air moving across the heating element or the atomizer as a whole when a user inhales on the electronic vaporizer). As noted above, to reliably activate the heating element or heat the heating element to a desired temperature, a vaporizer may, in some implementations of the current subject matter, make use of signals from a pressure sensor to determine when a user is inhaling. The pressure sensor can be positioned in the airflow path and/or can be connected (e.g., by a passageway or other path) to an airflow path connecting an inlet for air to enter the device and an outlet via which the user inhales the resulting vapor and/or aerosol such that the pressure sensor experiences pressure changes concurrently with air passing through the vaporizer device from the air inlet to the air outlet. In some implementations of the current subject matter, the heating element may be activated in association with a user's puff, for example by automatic detection of the puff, for example by the pressure sensor detecting a pressure change in the airflow path.

Typically, the pressure sensor (as well as any other sensors 113) can be positioned on or coupled (e.g., electrically or electronically connected, either physically or via a wireless connection) to the controller 104 (e.g., a printed circuit board assembly or other type of circuit board). To take measurements accurately and maintain durability of the vaporizer, it can be beneficial to provide a resilient seal 121 to separate an airflow path from other parts of the vaporizer. The seal 121, which can be a gasket, may be configured to at least partially surround the pressure sensor such that connections of the pressure sensor to internal circuitry of the vaporizer are separated from a part of the pressure sensor exposed to the airflow path. In an example of a cartridge-based vaporizer, the seal 121 may also separate parts of one or more electrical connections between a vaporizer body 110 and a vaporizer cartridge 120. Such arrangements of a seal 121 in a vaporizer 100 can be helpful in mitigating against potentially disruptive impacts on vaporizer components resulting from interactions with environmental factors such as water in the vapor or liquid phases, other fluids such as the vaporizable material, etc. and/or to reduce escape of air from the designed airflow path in the vaporizer. Unwanted air, liquid or other fluid passing and/or contacting circuitry of the vaporizer can cause various unwanted effects, such as alter pressure readings, and/or can result in the buildup of unwanted material, such as moisture, the vaporizable material, etc. in parts of the vaporizer where they may result in poor pressure signal, degradation of the pressure sensor or other components, and/or a shorter life of the vaporizer. Leaks in the seal 121 can also result in a user inhaling air that has passed over parts of the vaporizer device containing or constructed of materials that may not be desirable to be inhaled.

A general class of vaporizers that have recently gained popularity includes a vaporizer body 110 that includes a controller 104, a power source 112 (e.g., battery), one more sensors 113, charging contacts, a seal 121, and a cartridge receptacle 118 configured to receive a vaporizer cartridge 120 for coupling with the vaporizer body 110 through one or more of a variety of attachment structures. In some examples, vaporizer cartridge 120 includes a mouthpiece for delivering an inhalable dose to a user. The vaporizer body 110 can include an atomizer having a heating element 150, or alternatively, the heating element 150 can be part of the vaporizer cartridge 120.

As noted above, the current subject matter relates to cartridge-based configurations for vaporizers that generate an inhalable dose of a vaporizable material via heating of a source substance. For example, a vaporizer cartridge 120 may include a mass of a source substance that is processed and formed to have direct contact with parts of one or more resistive heating elements, and such a vaporizer cartridge 120 may be configured to be coupled mechanically and electrically to a vaporizer body 110 that includes a processor, a power source 112, and electrical contacts for connecting to corresponding cartridge contacts 124 for completing a circuit with the one or more resistive heating elements.

In vaporizers in which the power source 112 is part of a vaporizer body 110 and a heating element 150 is disposed in a vaporizer cartridge 120 configured to couple with the vaporizer body 110, the vaporizer 100 may include electrical connection features (e.g., means for completing a circuit) for completing a circuit that includes the controller 104 (e.g., a printed circuit board, a microcontroller, or the like), the power source 112, and the heating element 150. These features may include at least two contacts on one or more outer surfaces of the vaporizer cartridge 120 (referred to herein as cartridge contacts 124) and at least two contacts disposed on the vaporizer body 110, optionally in a cartridge receptacle 118 (referred to herein as receptacle contacts 125) of the vaporizer 100 such that the cartridge contacts 124 and the receptacle contacts 125 make electrical connections when the vaporizer cartridge 120 is inserted into and coupled with the cartridge receptacle 118. Other configurations in which a vaporizer cartridge 120 is coupled to a vaporizer body 110 without being inserted into a cartridge receptacle 118 are also within the scope of the current subject matter. It will be understood that the references herein to "receptacle contacts" can more generally refer to contacts on a vaporizer body 110 that are not contained within a cartridge receptacle 118 but are nonetheless configured to make electrical connections with the cartridge contacts 124 of a vaporizer cartridge 120 when the vaporizer cartridge 120 and the vaporizer body 110 are coupled. The circuit completed by these electrical connections can allow delivery of electrical current to the resistive heating element 150 and may further be used for additional functions, such as for example for measuring a resistance of the resistive heating element 150 for use in determining and/or controlling a temperature of the resistive heating element 150 based on a thermal coefficient of resistivity of the resistive heating element 150, for identifying a cartridge based on one or more electrical characteristics of a resistive heating element 150 or the other circuitry of the vaporizer cartridge 120, etc.

In some examples of the current subject matter, the at least two cartridge contacts 124 and the at least two receptacle contacts 125 can be configured to electrically connect in either of at least two orientations. In other words, one or more circuits necessary for operation of the vaporizer can be completed by insertion of a vaporizer cartridge 120 in the cartridge receptacle 118 in a first rotational orientation (around an axis along which the end of the vaporizer cartridge 120 having the cartridge is inserted into the cartridge receptacle 118 of the vaporizer body 110) such that a first cartridge contact of the at least two cartridge contacts 124 is electrically connected to a first receptacle contact of the at least two receptacle contacts 125 and a second cartridge contact of the at least two cartridge contacts 124 is electrically connected to a second receptacle contact of the at least two receptacle contacts 125. Furthermore, the one or more circuits necessary for operation of the vaporizer can be completed by insertion of a vaporizer cartridge 120 in the cartridge receptacle 118 in a second rotational orientation such that the first cartridge contact of the at least two cartridge contacts 124 is electrically connected to the second receptacle contact of the at least two receptacle contacts 125 and the second cartridge contact of the at least two cartridge contacts 124 is electrically connected to the first receptacle contact of the at least two receptacle contacts 125. This feature of a vaporizer cartridge 120 being reversibly insertable into a cartridge receptacle 118 of the vaporizer body 110 is described further below.

In one example of an attachment structure for coupling a vaporizer cartridge 120 to a vaporizer body 110, the vaporizer body 110 includes a detent (e.g., a dimple, protrusion, etc.) protruding inwardly from an inner surface of the cartridge receptacle 118. One or more exterior surfaces of the vaporizer cartridge 120 can include corresponding recesses (not shown in FIG. 1) that can fit and/or otherwise snap over such detents when an end of the vaporizer cartridge 120 is inserted into the cartridge receptacle 118 of the vaporizer body 110. When the vaporizer cartridge 120 and the vaporizer body 110 are coupled (e.g., by insertion of an end of the vaporizer cartridge 120 into the cartridge receptacle 118 of the vaporizer body 110), the detent into the vaporizer body 110 may fit within and/or otherwise be held within the recesses of the vaporizer cartridge 120 to hold the vaporizer cartridge 120 in place when assembled. Such a detent-recess assembly can provide enough support to hold the vaporizer cartridge 120 in place to ensure good contact between the at least two cartridge contacts 124 and the at least two receptacle contacts 125, while allowing release of the vaporizer cartridge 120 from the vaporizer body 110 when a user pulls with reasonable force on the vaporizer cartridge 120 to disengage the vaporizer cartridge 120 from the cartridge receptacle 118. It will be understood that other configurations for coupling of a vaporizer cartridge 120 and a vaporizer body 110 are within the scope of the current subject matter, for example as discussed in more detail below.

Further to the discussion above about the electrical connections between a vaporizer cartridge 120 and a vaporizer body 110 being reversible such that at least two rotational orientations of the vaporizer cartridge 120 in the vaporizer cartridge 120 receptacle are possible, in some vaporizer devices the shape of the vaporizer cartridge 120, or at least a shape of the end of the vaporizer cartridge 120 that is configured for insertion into the cartridge receptacle 118 may have rotational symmetry of at least order two. In other words, the vaporizer cartridge 120 or at least the insertable end of the vaporizer cartridge 120 may be symmetric upon a rotation of 180° around an axis along which the vaporizer cartridge 120 is inserted into the cartridge receptacle 118. In such a configuration, the circuitry of the vaporizer device may support identical operation regardless of which symmetrical orientation of the vaporizer cartridge 120 occurs.

In some examples, the vaporizer cartridge 120, or at least an end of the vaporizer cartridge 120 configured for insertion in the vaporizer cartridge 120 receptacle may have a non-circular cross-section transverse to the axis along which the vaporizer cartridge 120 is inserted into the cartridge receptacle 118. For example, the non-circular cross-section may be approximately rectangular, approximately elliptical (e.g., have an approximately oval shape), non-rectangular but with two sets of parallel or approximately parallel opposing sides (e.g., having a parallelogram-like shape), or other shapes having rotational symmetry of at least order two. In this context, approximately having a shape, indicates that a basic likeness to the described shape is apparent, but that sides of the shape in question need not be completely linear and vertices need not be completely sharp. Rounding of both or either of edges or vertices of the cross-sectional shape is contemplated in the description of any non-circular cross-section referred to herein.

The at least two cartridge contacts 124 and the at least two receptacle contacts 125 can take various forms. For example, one or both sets of contacts may include conductive pins, tabs, posts, receiving holes for pins or posts, or the like. Some types of contacts may include springs or other urging features to cause better physical and electrical contact between the contacts on the vaporizer cartridge 120 and the vaporizer body 110. The electrical contacts may optionally be gold-plated, and/or can include other materials.

Various embodiments of a vaporizer cartridge 120 are described herein that are configured for containing and vaporizing one or more non-liquid source substances, such as loose-leaf tobacco. Furthermore, such embodiments of vaporizer cartridges may be single-use such that they are not refillable after the vaporizable material has been used up. Such single-use vaporizer cartridges may thus require inexpensive material and manufacturing in order to be economically feasible. Furthermore, although it may be desirable to make and manufacture single-use vaporizer cartridges for vaporizing non-liquid source substances, it is also desirable to efficiently and effectively vaporize the vaporizable material. For example, a user inhaling on a vaporizer device typically prefers inhaling aerosol created by the vaporizer device shortly after engaging with the vaporizer device (e.g., placing lips on mouthpiece, pushing an activation button, etc.). As such, the embodiments of the vaporizer cartridges disclosed herein may beneficially achieve efficient vaporization of vaporizable material from a source substance to achieve a desired user experience. Furthermore, embodiments of the vaporizer cartridge 120 disclosed herein may advantageously provide sufficient heat energy to the source substance to cause release of the vaporizable material such as to create an aerosol form of the vaporizable material for inhalation, while also limiting heating sufficiently to at least reduce creation of at least one harmful by-product that is not desired for a user to inhale. To achieve the above, various embodiments of heating elements are disclosed and described in greater detail below.

For example, various embodiments of heating elements are described herein that are configured to heat within a desired temperature range, such as at or below approximately 250 degrees Celsius. Such a temperature range may advantageously vaporize a source substance such as processed tobacco and allow nicotine and volatile flavor compounds to be aerosolized and delivered to a user puffing on the associated vaporization device. Such a temperature within the temperature range may also prevent the creation of at least one harmful or potentially harmful by-product. As such, at least one benefit of the heating assemblies described herein include the improved quality of aerosol for inhalation by a user.

In addition, various embodiments of the heating elements described herein may efficiently heat up to a temperature within the desired temperature range. This can allow the associated vaporizer device to achieve a desired user experience for the user inhaling on the vaporizer device. Such efficient heat-up time can result in efficient power usage, such as battery power from the vaporizer device. Furthermore, the various embodiments of the heating elements described herein can achieve such benefits while not requiring an increase in vaporizer device size. In some embodiments, the heating element can allow for a more compact vaporizer device than what is currently available. In addition, embodiments of the heating element can be made and manufactured at a cost that may allow the vaporizer cartridge to be single-use and economically feasible.

Embodiments of the heating elements described below can include at least one thermally conductive material, such as carbon, carbon foam, metal, metal foil, aluminum foam, or a biodegradable polymer. The thermally conductive material can allow energy provided by a vaporizer device to be transmitted to the thermally conductive feature (e.g., via the cartridge and vaporizer device contacts) to thereby cause an increase in temperature along at least a part of the thermally conductive feature, such as for vaporizing the vaporizable material from the source substance. The vaporizer body 110 can include a controller 104 that can control the amount of energy provided to the thermally conductive material, thereby assisting the heating element 150 with reaching a temperature that is within the desired temperature range.

In some embodiments, a vaporizer cartridge can include a housing 162 configured to contain at least some of the vaporizable material 102 and/or heating element 150.

Figure 2A:
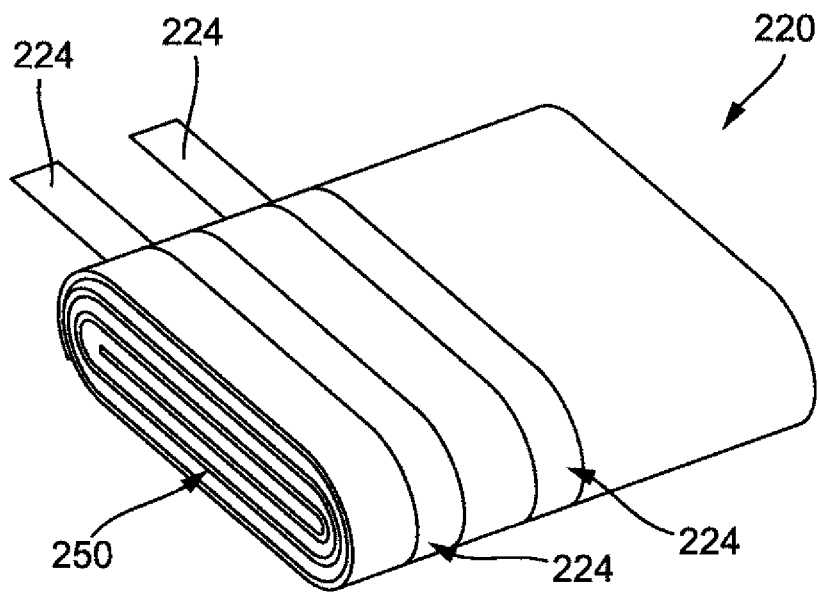
FIG. 2A illustrates a perspective view of an embodiment of a vaporizer cartridge including an embodiment of a heating element having a flexible sheet with narrow conductive traces extending therealong.
Figure 2B:
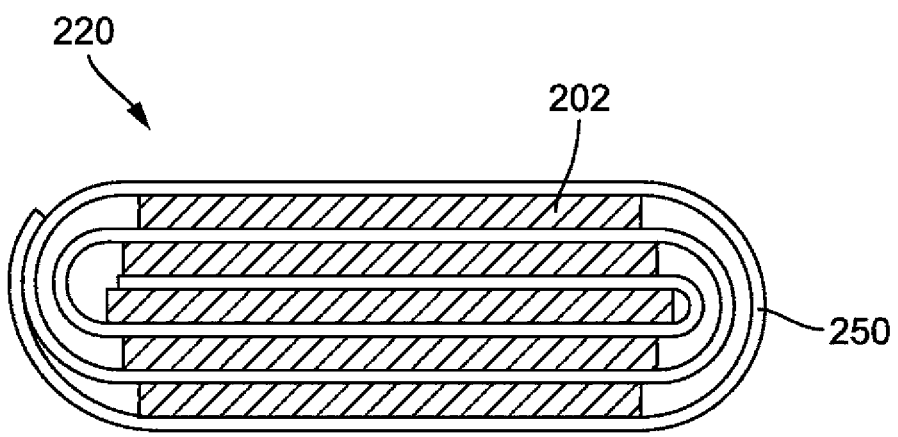
FIG. 2B illustrates an end view of the vaporizer cartridge of FIG. 2A showing the flexible sheets of the heating element wrapped around non-liquid vaporizable material.

FIGS. 2A-2B illustrate an embodiment of a vaporizer cartridge 220 including an embodiment of a heating element 250 including a flexible sheet with narrow electrically conductive traces 252 extending therealong. These narrow electrically conductive traces 252 form resistive heaters, which can be arranged in series or parallel. The narrow electrically conductive traces 252 can be made out of an electrically conductive material, such as any of the electrically conductive materials described herein. The heating element 250 can include at least one cartridge contact 224 that is in electrical communication with the narrow electrically conductive traces. The cartridge contacts 224 can be positioned such that when the vaporizer cartridge 220 is coupled to a vaporizer body, the cartridge contacts 224 can mate with the receptacle contacts 125 (shown in FIG. 1) of the vaporizer body. This can allow energy from the vaporizer body to be transferred from the vaporizer body to the narrow electrically conductive traces 224 (via the contact between the cartridge contacts 224 and the receptacle contacts 125) thereby allowing the narrow electrically conductive traces 252 to reach a temperature within the desired temperature range.

In some embodiments, the flexible sheet can wrap around non-liquid source substance 202, such as a plurality of sheets of tobacco, as shown in FIG. 2B. In such a configuration, the heating element 250 can both define a chamber configured to contain the source substance 202, as well as be contained within the chamber. This can increase the contact between the source substance 202 and the heating element 150, thereby allowing the heating element 150 to efficiently heat up and vaporize the vaporizable material from the source substance 202. Furthermore, a thermal gradient across the source substance 202 can be minimal (e.g., less than or equal to the width of a tobacco sheet) in such a configuration. This can allow the heating element 150 to heat to a temperature within the desired temperature range while also efficiently vaporizing an acceptable fraction (ideally but not necessarily all or substantially all) of the vaporizable material contained within the source substance 202 in the chamber.

Figure 2C:
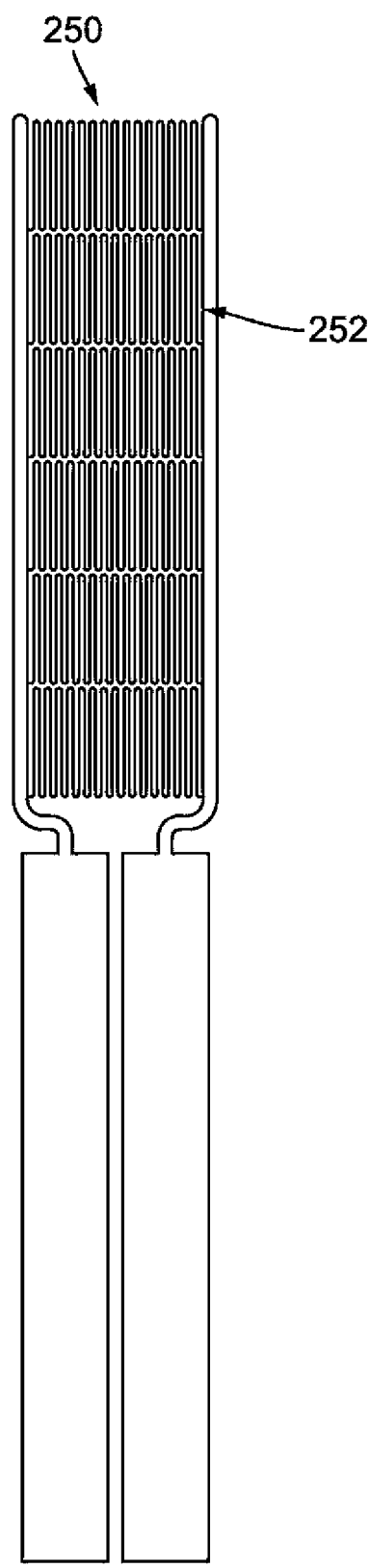
FIG. 2C illustrates a top view of an embodiment of the heating element of FIG. 2A showing a plurality of narrow conductive traces forming six series heaters in parallel, and with each series heater portion in a horizontal orientation.
Figure 2D:
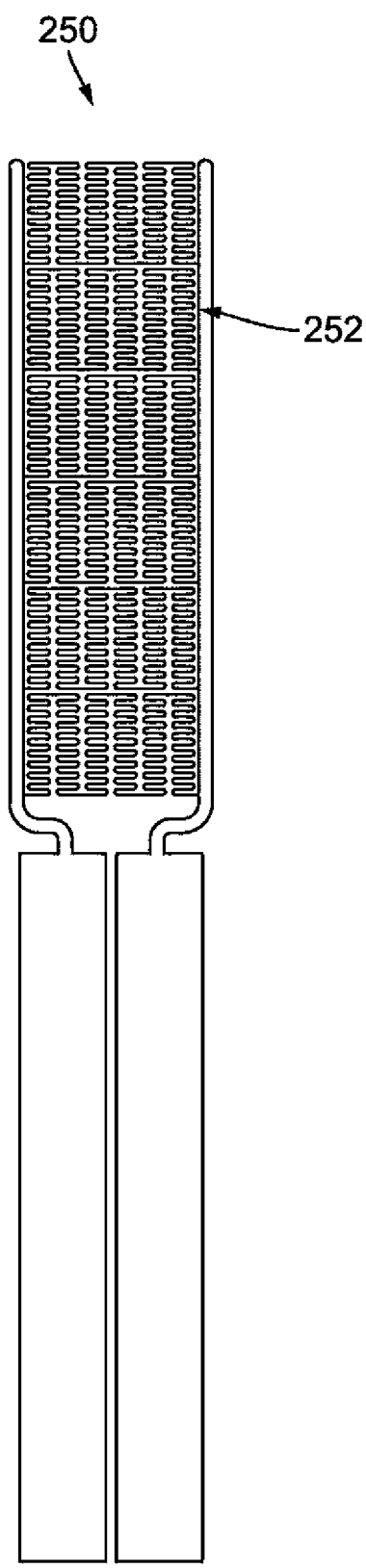
FIG. 2D illustrates a top view of an embodiment of the heating element of FIG. 2A showing a plurality of narrow conductive traces forming six series heaters in parallel, and with each series heater portion in a vertical orientation.

FIGS. 2C and 2D illustrate embodiments of the narrow electrically conductive traces 252 of the heating element 150. For example, as shown in FIGS. 2C and 2D, the narrow electrically conductive traces 252 can include a plurality of series heaters in parallel, such as six series heaters positioned in parallel. Additionally, as shown in FIG. 2C, each series heater can be laid out in a horizontal orientation and/or in a vertical orientation, as shown in FIG. 2D. For example, the horizontal orientation can provide a series resistance of approximately 2.18 Ohm at 25° C. and 4.09 Ohm at 250° C. and total heater resistance of approximately 0.363 Ohm at 25° C. and 0.682 Ohm at 250° C. In the vertical orientation, for example, the series resistance of approximately 2.14 Ohm at 25° C. and 4.02 Ohm at 250° C. and total heater resistance of approximately 0.357 Ohm at 25° C. and 0.670 Ohm at 250° C. Other configurations of the narrow electrically conductive traces are within the scope of this disclosure. FIG. 2C illustrates the heating element 150 of FIG. 2A with the narrow electrically conductive traces 252 forming six series heaters in parallel, and with each series heater portion in a horizontal orientation FIGS. 3A-3B illustrates another embodiment of a vaporizer cartridge 320 including another embodiment of a heating element 350 (shown in FIG. 3B) that allows the vaporizer cartridge 320 to include at least some of the benefits described herein, including cost effective manufacturing, fast heat-up time, vaporization temperatures within the desired temperature range, etc.

Figure 3A:
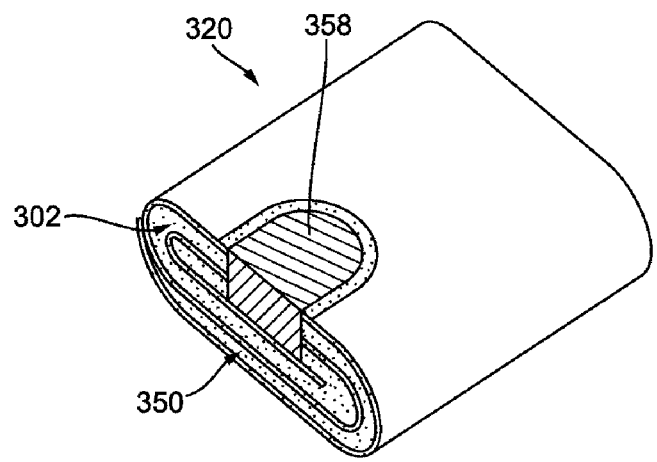
FIG. 3A illustrates a top perspective view of another embodiment of the vaporizer cartridge including another embodiment of the heating element including a perforated conductive material having differential resistance areas.
Figure 3B:
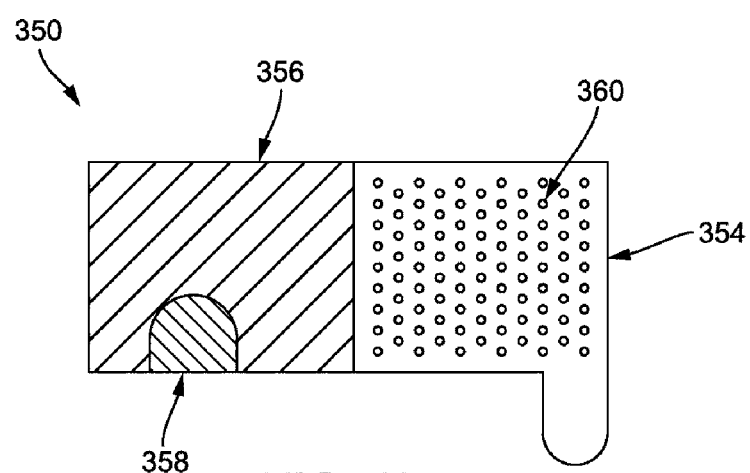
FIG. 3B illustrates a top view of the heating element of FIG. 3A including an electrically resistive area having a plurality of perforations.

As shown in FIG. 3B, the heating element 350 includes an electrically resistive area 354 made out of an electrically conductive material, such as an electrically conductive foil material treated to increase its electrical resistance in a desired part of the electrically conductive foil (e.g., by perforating, varying a thickness or other dimension of a conducive cross-section, etc.). In some embodiments, a first part of the electrically resistive area 354 can include a non-conductive material backing 356 (e.g., paper material) and a second part of the electrically resistive area 354 can include the electrically resistive material 358 without the non-conductive material backing 356. In addition, and as noted above, the second part can include a plurality of perforations 360, which can create an electrical resistance along an otherwise more electrically conductive material of the second part. The perforations 360 can have any number of a variety of shapes and sizes and be arranged in one or more of a variety of configurations. Furthermore, the electrically resistive second part can be an electrically conductive material that includes more than one area having different densities of perforations 360 or other physical modifications, thereby creating different areas of electrical resistance. Such different areas of electrical resistance can affect the temperature reached when the electrically resistive part is caused to be heated (e.g., an electrical current is allowed to travel along). As shown in FIGS. 3A and 3B, a part of the heating element 350 can include only a non-electrically conductive material, such as a part of the heating element 350 that may allow contact with a user and therefore may benefit from not becoming heated. Other configurations are also within the scope of this disclosure, such as heating elements having one or more areas including electrically conductive material without perforations, such as for forming a cartridge contact that may mate with a vaporizer contact for allowing current to be transferred from the vaporizer device to the heating element for heating the heating element.

As shown in FIG. 3A, the heating element 350 can be wrapped around a source substance 302, such as a non-liquid source substance (e.g., one or more sheets of tobacco). In such a configuration, the heating element 350 can both define a chamber configured to contain the source substance 302, as well as be contained within the cartridge chamber. This can increase the contact between the source substance 302 and the heating element 350, thereby allowing the heating element 350 to efficiently heat up and vaporize vaporizable material from the source substance 302. Furthermore, a thermal gradient across the source substance 302 can be reduced (e.g., less than or equal to the width of a tobacco sheet) in such a configuration. This can allow the heating element 350 to heat to a temperature within the desired temperature range while also efficiently vaporizing an acceptable fraction (ideally but not necessarily all or substantially all) of the vaporizable material contained within the source material in the chamber.

FIGS. 4A-4E illustrate another embodiment of a vaporizer cartridge 420 including another embodiment of a heating element 450 (shown, for example, in FIG. 4B) that allows the vaporizer cartridge 420 to include at least some of the benefits described herein, including cost effective manufacturing, fast heat-up time, vaporization temperatures within the desired temperature range, etc.

As shown in FIG. 4A, the vaporizer cartridge 420 can include a housing 462 having an opening 464 for receiving the heating element 450 and source substance 402. The housing 462 can include a non-electrically conductive material and the heating element 450 can include a sheet 448 made out of thermally conductive material. As shown in FIG. 4B, the sheet 448 can include a plurality of perforations 460 that can affect the resistance along the sheet 448. In addition, the sheet can include at least one side extension forming cartridge contacts 424 that can mate with and extend through a through hole 428 along the housing 462. Such a side extension forming cartridge contacts 424 can be positioned to mate with a receptacle contact along a corresponding vaporizer body thereby allowing current to flow from the vaporizer body to the heating element 450 in turn allowing the heating element 450 to heat to a temperature within the desired temperature range.

Figure 4D:
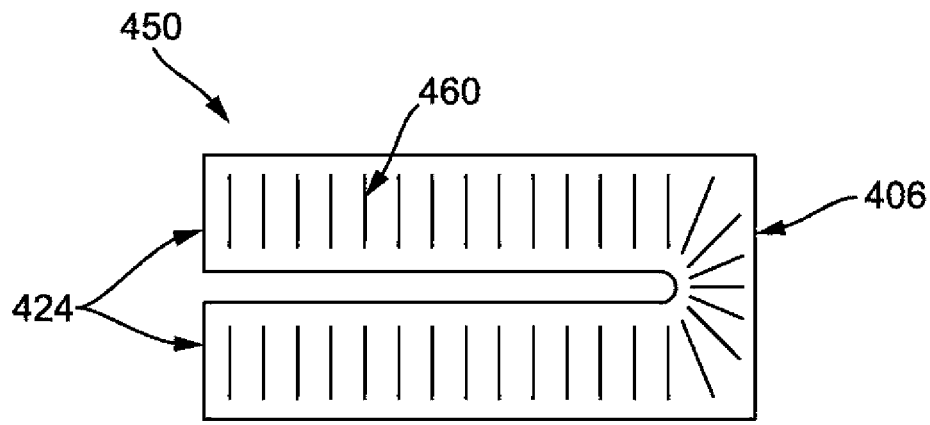
FIG. 4D illustrates a top view of another embodiment of the heating element of FIG. 4B including a slit extending along a length of the heating element and intersecting an end of the heating element.
Figure 4E:
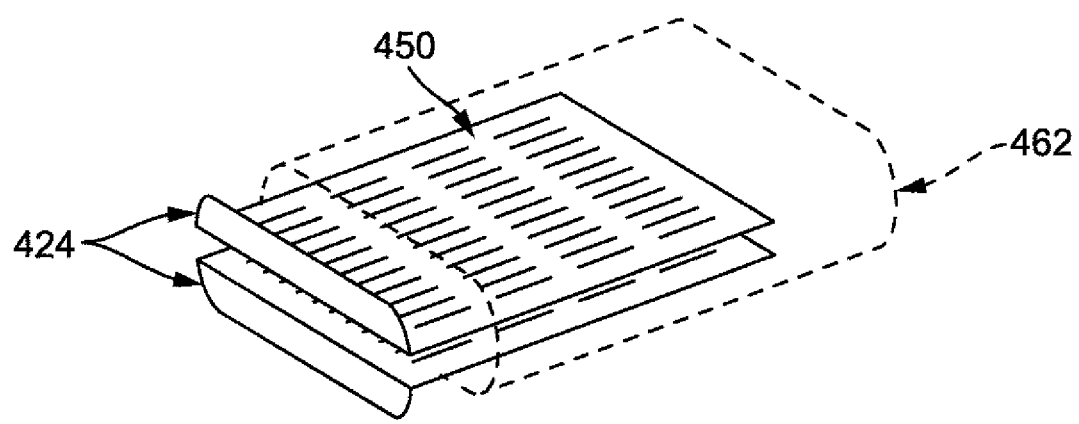
FIG. 4E illustrates a perspective view of the heating element of FIG. 4D showing the heating element folded long at least the slit.

As shown in FIG. 4C, the heating element 450 may include at least one flat surface in which the source substance 402 can mate directly against, thereby providing efficient heat transfer between the heating element 450 and the source substance 402 (e.g., one or more sheets of tobacco). Furthermore, a thermal gradient across the source substance 402 can be minimal (e.g., less than or equal to the width of a tobacco sheet) in such a configuration. This can allow the heating element 450 to heat to a temperature within the desired temperature range while also efficiently vaporizing all or substantially all of the vaporizable material contained within the source substance 402 within the chamber. Other variations and/or features of the heating element 450 can be included, such as folding the heating element 450 in half with cartridge contacts 424 extending from a distal end (as shown in FIG. 4E), and/or include an etched electrically conductive sheet 406 that is effectively long and thin for resulting in electrical resistance sufficient to achieve fast and effective heating of the heating element 450 to within the desired heating range (as shown, for example, in FIG. 4D).

Figure 4F:
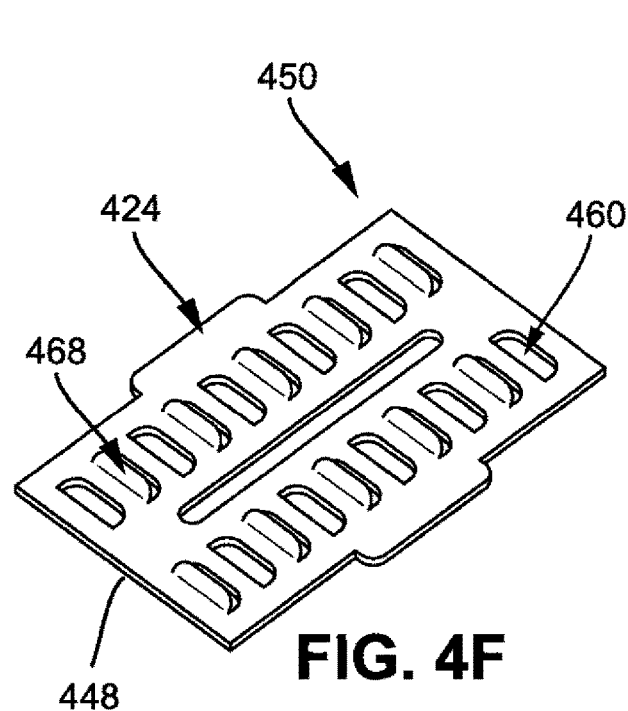
FIG. 4F illustrates a perspective view of another embodiment of the heating element of FIG. 4B including at least one extension extending from a top side and/or a bottom side of the sheet of the heating element.
Figure 4G:
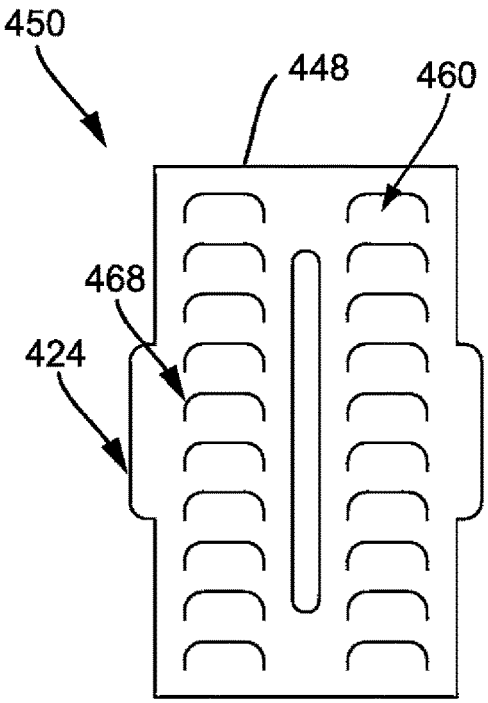
FIG. 4G illustrates a top view of the heating element of FIG. 4F.
Figure 4H:
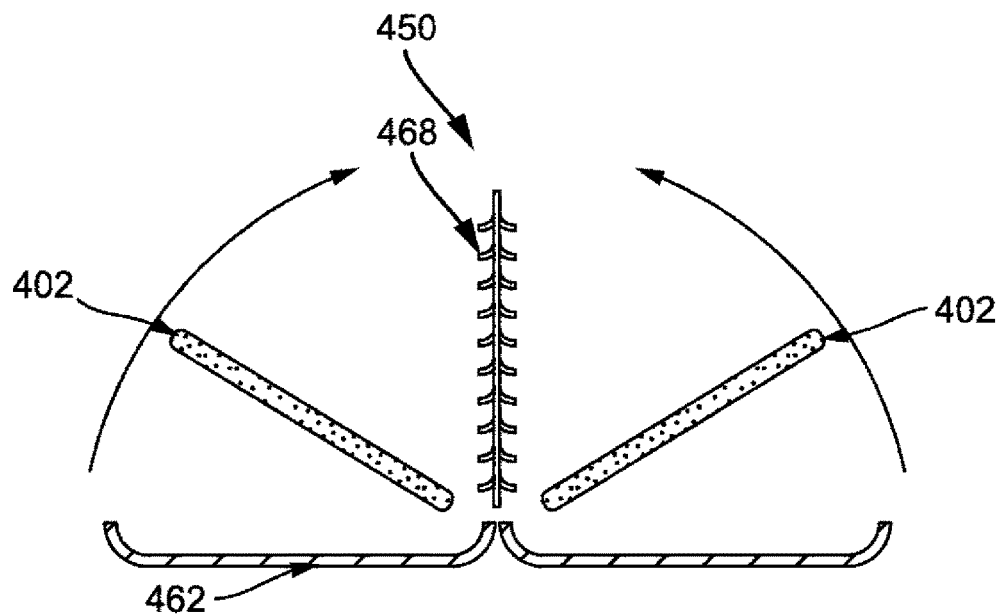
FIG. 4H illustrates an embodiment of a vaporizer cartridge housing for securing the heating element of FIG. 4F and non-liquid vaporizable material therewithin.

In some embodiments, as shown in FIGS. 4F and 4G, one or more extensions 468 can extend from a top and/or bottom surface of the thermally conductive sheet 448. Such extensions 468 can be formed when forming the perforations 460 (e.g., via stamping the conductive sheet). The extensions 468 can provide additional surface area that may be more integrated with the source substance 402, such as compared to a flat heating element that does not include such extensions. As shown in FIG. 4H, some embodiments of the housing 462 can include a clamshell configuration such that the heating element 450 (e.g., any of the heating element embodiments shown in FIGS. 4A-4G) can be captured in the housing 462 along with at least two tobacco sheets positioned on opposing sides of the heating element 450. This can provide a compact configuration with efficient assembly.

Figure 5A:
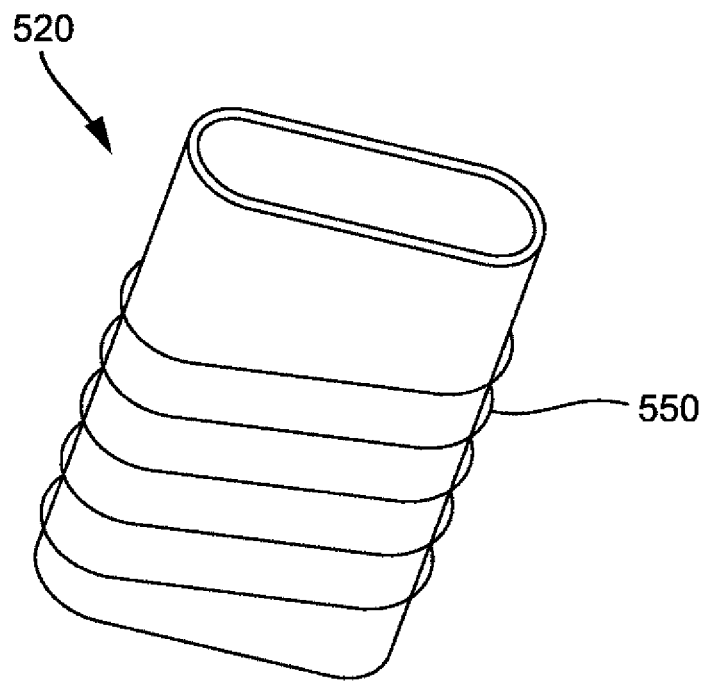
FIG. 5A illustrates a top perspective view of another embodiment of a vaporizer cartridge including another embodiment of a heating element including an induction coil and ferrous material.
Figure 5B:
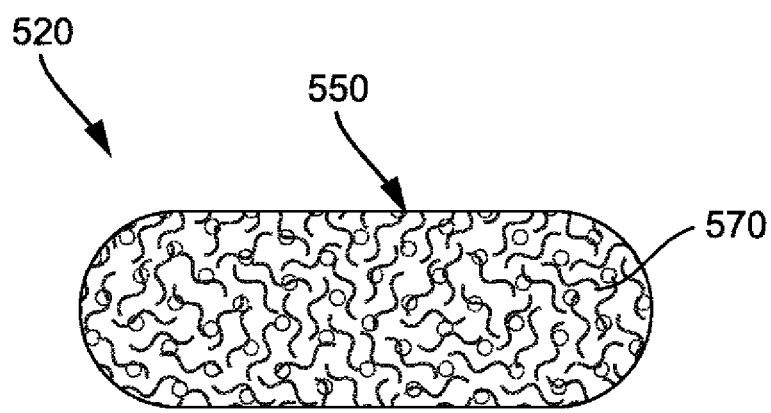
FIG. 5B illustrates an end view of the vaporizer cartridge of FIG. 5A showing the ferrous material interspersed in non-liquid vaporizable material.

FIGS. 5A-5B illustrates another embodiment of a vaporizer cartridge 520 including another embodiment of a heating element 550 having an induction coil and ferrous material 570. For example, the induction coil can be wrapped around the source substance, such as directly around a sheet of source substance. In addition, the ferrous material 570 may be mixed with the source substance and may be heated as a result of interaction of the ferrous material with electrical and/or magnetic fields created by current passing through the inductive coil. The ferrous material inter-mixed with the source substance can allow a more even distribution of heat along and/or within the source substance, thereby reducing a thermal gradient along the source substance. This can allow heating of the source substance under interaction of the fields generated by the induction coil to a temperature within the desired temperature range and thereby effectively vaporize vaporizable material from the source substance.

Figure 6:
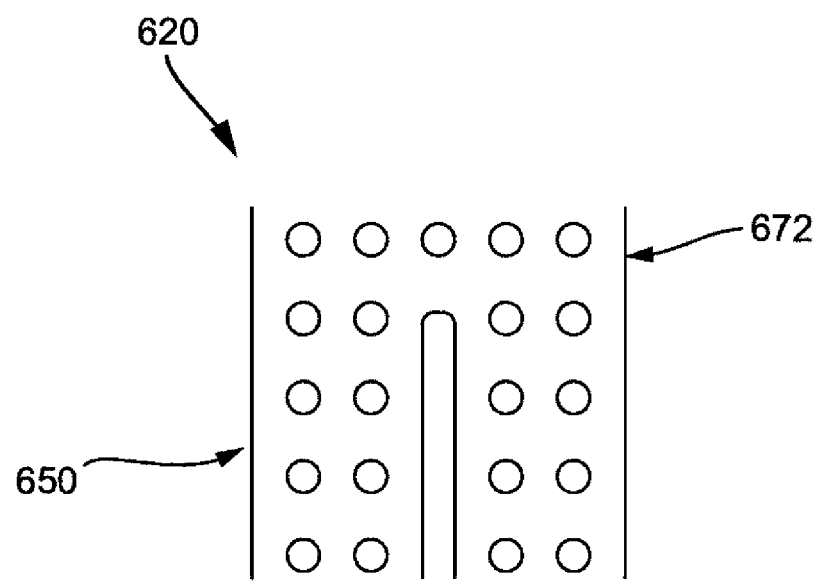
FIG. 6 illustrates a side cross-section view of another embodiment of a vaporizer cartridge including another embodiment of a heating element having an electrically resistive foam structure.

FIG. 6 illustrates a side cross-section view of another embodiment of a vaporizer cartridge 620 including another embodiment of a heating element 650 having a thermally conductive (but electrically resistive) foam structure 672. For example, the source substance may be placed into the conductive foam structure 672 (e.g., within pores of an open-cell thermally conductive foam structure). Current can be run through the thermally conductive foam structure 672 to thereby evenly heat the source substance as a result of resistive heating of the thermally conductive foam structure 672, such as at a temperature within the desired temperature range. In some embodiments, the thermally conductive foam structure 672 can be made out of a reticulated carbon foam, an aluminum foam, etc. Other foam structures are within the scope of this disclosure.

Figure 7:
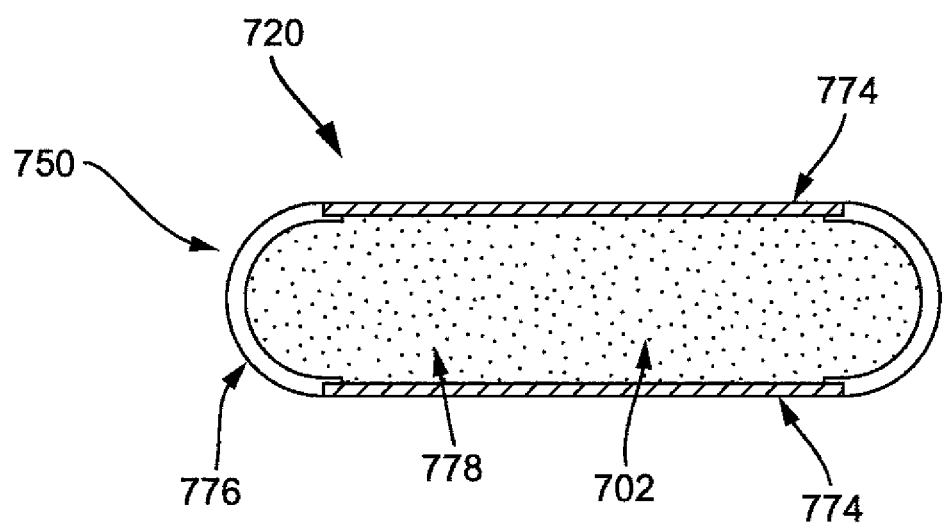
FIG. 7 illustrates another embodiment of a vaporizer cartridge including another embodiment of a heating element having electrically conductive plates separated by an insulating material and an at least partially electrically conductive mixture.

FIG. 7 illustrates another embodiment of a vaporizer cartridge 720 including another embodiment of a heating element 750 having conductive plates 774 separated by a non-conductive insulating material 776. The conductive plates 774 and insulating material 776 can define a chamber configured to contain source substance 702. The heating element 750 can further include an at least partially electrically conductive mixture 778 that can be included in the source substance 702, thereby creating a bulk resistor out of the source substance 702. The conductive plates 774 may function to conduct electricity and act as cartridge contacts that mate with receptacle contacts of the vaporizer body to which the vaporizer cartridge 720 is coupled.

Any of the heating elements described herein can include a contact (e.g., a cartridge contact) or can be in electrical communication with a contact for allowing electrical energy to be transmitted from a vaporizer body to which the vaporizer cartridge is coupled thereto and thereby allow the heating element to increase in temperature.

To vaporize vaporizable material from the source substance without having to heat above the desired temperature range, a reverse flow heat exchanger may be implemented into a vaporizer cartridge or vaporizer device. For example, a vaporizer cartridge including a reverse flow heat exchanger is described in greater detail below.

Figure 8A:
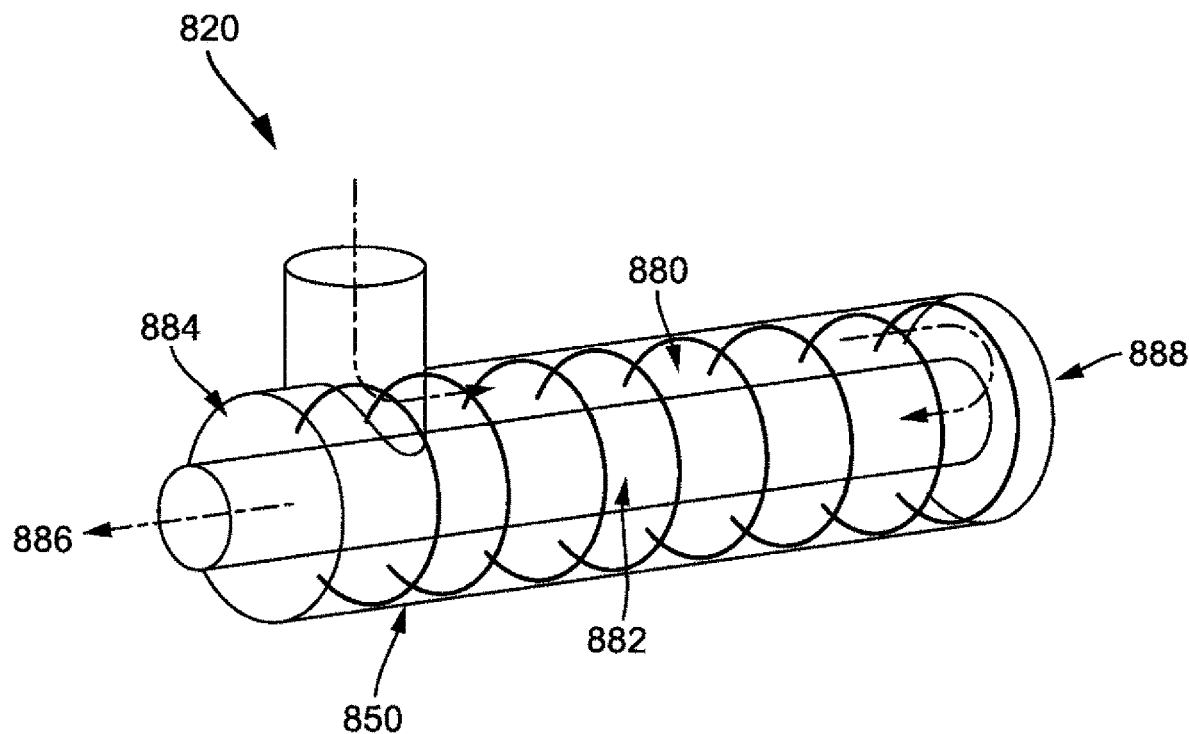
FIG. 8A illustrates a perspective view of another embodiment of a vaporizer cartridge.
Figure 8B:
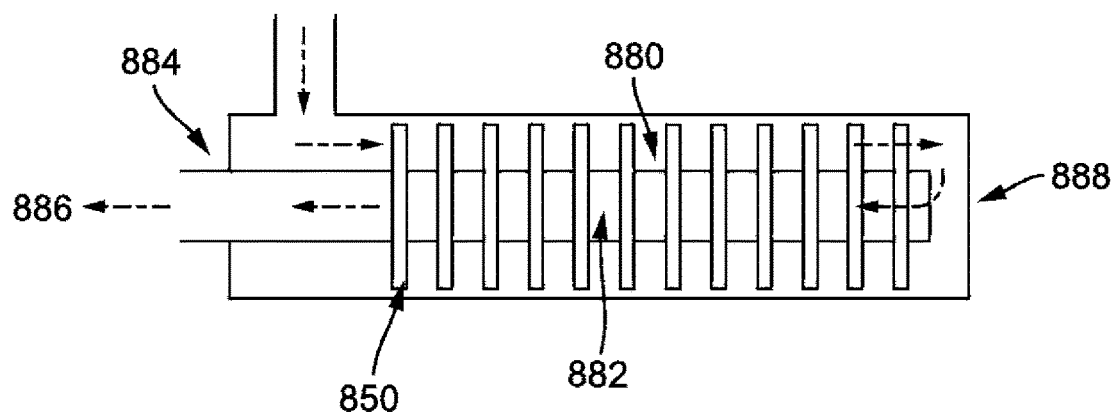
FIG. 8B illustrates a cross-sectional schematic view of the vaporizer cartridge of FIG. 8A.

FIGS. 8A-8B illustrate another embodiment of a vaporizer cartridge 820 including another embodiment of a heating element 850. As shown in FIG. 8A, a thermally conductive material can encircle an outer circumference of an outer source substance passageway 880. The outer source substance passageway 880 can include a doughnut-shaped profile where the inner through-hole defines an inner source substance passageway 882. As shown in FIG. 8B, the inner source substance passageway 882 may be open at a distal end 884 and the outer source substance passageway 880 may include an opening at a distal end 884. The inner and outer source substance passageways may be at least partly filled with source substance. An airflow pathway 886 can extend between the opening to the outer source substance passageway 880, along at least a part of the source substance passageway, through a proximal end 888 of the inner source substance passageway 882, along the inner source substance passageway 882 and out the distal opening of the source substance passageway, as shown in FIG. 8B. This can allow airflow (e.g., as a result of a user inhaling on the vaporizer device) to flow along the outer source substance passageway 880, thereby becoming heated by thermally conductive material encircling the outer circumference of the source substance passageway. As such, when the heated airflow then flows along the inner source substance passageway 882, the heated airflow can increase the temperature of the source substance positioned along the inner source substance passageway 882. This can assist with increasing the speed at which the source substance contained in the inner source substance passageway heats to the desired temperature (e.g., within the desired temperature range) and reducing the temperature gradient throughout the source substance.

At least some of the advantages of this concept may include a reduction in peak temperatures along the source substance that are greater than the desired temperature range. As such, this may result in at least a reduction in unwanted bi-products being created while vaporizing vaporizable material from the source substance. Additionally, since there is no direct contact between the source substance and the vaporizer device, minimal maintenance (e.g., cleaning, etc.) of the vaporizer device may be required.

Although the heating element and airflow passageway is described herein as being included in a vaporizer cartridge, any one or more parts of the heating element and airflow passageway described herein can be included in the vaporizer device, thereby configured to be reusable and durable.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A cartridge for a vaporizer device, the cartridge comprising:
   a chamber configured to contain a non-liquid vaporizable material;
   a heating element comprising an electrically resistive material and configured to vaporize the vaporizable material by delivery of heat to the vaporizable material, wherein at least a portion of the heating element defines a part of the chamber and/or is contained within the chamber;
   a cartridge contact in electrical communication with the electrically resistive material, the cartridge contact configured to couple to a vaporizer contact positioned proximate to a cartridge coupling feature to allow electrical power to pass from the vaporizer device through the electrically resistive material, the electrical power causing heating of the electrically resistive material and the vaporizable material to result in generation of an aerosol for inhalation by a user;
   wherein the heating element includes a flexible printed circuit including the electrically resistive material traced on a flexible material, and wherein the traced electrically resistive material forms a plurality of series heaters.

2. The cartridge of claim 1, wherein the heating element comprises the cartridge contact.

3. The cartridge of claim 1, wherein the heating element comprises a non-electrically conductive area.

4. The cartridge of claim 1, wherein the plurality of series heaters are positioned in parallel.

5. The cartridge of claim 1, further including a housing comprising a non-electrically conductive material and containing at least a part of the chamber.

6. The cartridge of claim 1, wherein the electrically resistive material extends along a length of the flexible material.

7. The cartridge of claim 1, wherein the vaporizable material includes nicotine.

8. The cartridge of claim 1, wherein the plurality of series heaters are positioned in a horizontal orientation.

9. A method for generating an inhalable aerosol, the method comprising:
   coupling a cartridge contact of a vaporizer cartridge to a vaporizer contact of a vaporizer device body to provide an electrically conductive pathway between a power source of the vaporizer device body and a heating element of the vaporizer cartridge, the electrically conductive pathway allowing the power source to cause heating of an electrically resistive material of the heating element and a vaporizable material contained in a chamber of the vaporizer cartridge; and
   heating the heating element to vaporize the vaporizable material and form an aerosol for inhalation, wherein the heating element defines at least a part of the chamber and/or is contained within the chamber of the vaporizer cartridge;
   wherein the heating element includes a flexible printed circuit including the electrically resistive material traced on a flexible material, and wherein the traced electrically resistive material forms a plurality of series heaters.

10. A cartridge for a vaporizer device, the cartridge comprising:
    a chamber configured to contain a non-liquid vaporizable material;
    a heating element comprising an electrically resistive material and configured to vaporize the vaporizable material by delivery of heat to the vaporizable material, wherein at least a portion of the heating element defines a part of the chamber and/or is contained within the chamber;
    a cartridge contact in electrical communication with the electrically resistive material, the cartridge contact configured to couple to a vaporizer contact positioned proximate to a cartridge coupling feature to allow electrical power to pass from the vaporizer device through the electrically resistive material, the electrical power causing heating of the electrically resistive material and the vaporizable material to result in generation of an aerosol for inhalation by a user;
    wherein the heating element comprises a sheet of thermally conductive, electrically resistive material and wherein the sheet of thermally conductive, electrically resistive material comprises a first area having a first density of perforations and a second area having a second density of perforations that is greater than the first density of perforations.

11. The cartridge of claim 10, wherein the sheet of thermally conductive, electrically resistive material comprises at least one of a flexible material, a deformable material, and a rigid material.

12. The cartridge of claim 10, wherein the sheet of thermally conductive, electrically resistive material further includes at least one extension extending away from at least one of a top surface of the sheet of thermally conductive, electrically resistive material and a bottom surface of the sheet of thermally conductive, electrically resistive material.

13. The cartridge of claim 10, wherein the sheet of thermally conductive, electrically resistive material further comprises a third area with a non-conductive material backing.

14. The cartridge of claim 10, wherein the sheet of thermally conductive, electrically resistive material comprises a treated electrically conductive foil.

15. A system for a generating an inhalable aerosol comprising:
   a cartridge comprising:
      a chamber configured to contain a non-liquid vaporizable material;
      a heating element comprising an electrically resistive material and configured to vaporize the vaporizable material by delivery of heat to the vaporizable material, wherein at least a portion of the heating element defines a part of the chamber and/or is contained within the chamber; and
      a cartridge contact in electrical communication with the electrically resistive material, the cartridge contact configured to couple to a vaporizer contact positioned proximate to a cartridge coupling feature to allow electrical power to pass from a vaporizer device through the electrically resistive material, the electrical power causing heating of the electrically resistive material and the vaporizable material to result in generation of an aerosol for inhalation by a user;
      wherein the heating element includes a flexible printed circuit including the electrically resistive material traced on a flexible material, and wherein the traced electrically resistive material forms a plurality of series heaters; and
   a device body comprising:
      a cartridge receptacle for receiving the cartridge; and
      the vaporizer contact configured to mate with the cartridge contact when the cartridge is inserted into the cartridge receptacle to provide an electrically conductive pathway between a power source in the device body and the heating element of the cartridge.

16. The system of claim 15, wherein the heating element comprises the cartridge contact.

17. The system of claim 15, wherein the heating element comprises a sheet of thermally conductive, electrically resistive material.

18. The system of claim 17, wherein the sheet of thermally conductive, electrically resistive material comprises at least one of a flexible material, a deformable material, and a rigid material.

19. The system of claim 17, wherein the sheet of thermally conductive, electrically resistive material includes at least one perforation.

20. The system of claim 17, wherein the sheet of thermally conductive, electrically resistive material further includes at least one extension extending away from at least one of a top surface of the sheet of thermally conductive, electrically resistive material and a bottom surface of the sheet of thermally conductive, electrically resistive material.

* * * * *